(12) United States Patent
Eini et al.

(10) Patent No.: US 6,348,229 B1
(45) Date of Patent: Feb. 19, 2002

(54) FOOD COMPRISING THIXOTROPIC COMPOSITION OF UNSATURATED FAT AND PROCESS FOR MANUFACTURE THEREOF

(75) Inventors: Meir Eini, Ness Ziona; Dov Tamarkin, Maccabim, both of (IL)

(73) Assignee: Thixo Ltd., Ness Ziona (IL)

( * ) Notice: Subject to any disclaimer, the term of this patent is extended or adjusted under 35 U.S.C. 154(b) by 0 days.

(21) Appl. No.: 09/526,509

(22) Filed: Mar. 16, 2000

(30) Foreign Application Priority Data

Jan. 10, 2000 (IL) .................................................. 133969

(51) Int. Cl.[7] .............................................. A23D 9/007
(52) U.S. Cl. ........................ 426/611; 426/601; 426/607
(58) Field of Search ................................ 426/611, 601, 426/607; 554/227, 230; 424/439; 514/786, 787

(56) References Cited

U.S. PATENT DOCUMENTS

| | | | | |
|---|---|---|---|---|
| 3,519,436 A | * | 7/1970 | Bauer | |
| 4,127,679 A | * | 11/1978 | Amano et al. | 426/565 |
| 4,231,802 A | * | 11/1980 | McGinley et al. | 426/456 |
| 4,284,655 A | * | 8/1981 | Miller et al. | 426/602 |
| 4,388,339 A | * | 6/1983 | Lomneth et al. | 426/602 |
| 4,447,462 A | * | 5/1984 | Tafuri et al. | 426/601 |
| 5,023,102 A | * | 6/1991 | Given | 426/610 |
| 5,492,713 A | * | 2/1996 | Sommermeyer | 426/601 |
| 5,660,865 A | * | 8/1997 | Pedersen | 426/99 |
| 6,013,291 A | * | 1/2000 | Glass | 426/93 |
| 6,022,578 A | * | 2/2000 | Miller | 426/603 |
| 6,031,118 A | * | 2/2000 | van Amerongen et al. | 426/602 |
| 6,106,886 A | * | 8/2000 | van Amerongen et al. | 426/611 |
| 6,117,475 A | * | 9/2000 | van Amerongen et al. | 426/601 |
| 6,117,476 A | * | 9/2000 | Eger et al. | 426/601 |
| 6,123,979 A | * | 9/2000 | Hepburn et al. | 426/611 |
| 6,129,944 A | * | 10/2000 | Tiainen et al. | 426/577 |
| 6,156,369 A | * | 12/2000 | Eger et al. | 426/601 |
| 6,190,720 B1 | * | 2/2001 | Yuan et al. | 426/601 |
| 6,231,915 B1 | * | 5/2001 | van Amerongen et al. | 426/611 |
| 6,235,795 B1 | * | 5/2001 | Hernandez | 514/724 |

* cited by examiner

*Primary Examiner*—Carolyn Paden

(57) ABSTRACT

The present invention relates to food products having a thixotropic composition containing an unsaturated oil in high proportion and to the process of preparing a food product comprising an thixotropic unsaturated oil composition or having such a thixotropic composition applied thereto to produce a coated food product.

86 Claims, No Drawings

FOOD COMPRISING THIXOTROPIC COMPOSITION OF UNSATURATED FAT AND PROCESS FOR MANUFACTURE THEREOF

FIELD OF THE INVENTION

The present invention relates to food products comprising a thixotropic composition containing an unsaturated oil in high proportion and to the process of preparing a food product comprising a thixotropic unsaturated oil composition or having such a thixotropic composition applied thereto to produce a coated food product. More particularly the present invention relates to the use of a thixotropic composition in a process for the use of fat as a food additive or coating, wherein the fat is composed of an unusually high proportion of unsaturated oils. The process is suitable for optionally applying adjunctive ingredients such as flavoring, vitamins, and therapeutic substances to food.

BACKGROUND OF THE INVENTION

An even application of an oily substance is important in order to protect food from moisture as e.g. in the case of pastry and meat, or to protect it from loosing moisture as e.g. in the case of popcorn kernels. Moreover, such oils can serve as a delivery system for flavoring and therapeutic additives onto the food.

Oil must be in a solid phase in order to stick to the food. It must also be solid in order to facilitate even delivery and distribution of flavoring and therapeutic additives. For that purpose, oils are generally being hydrogenated, to obtain solid consistency, however, this process involved chemical change in the oil, namely complete or partial saturation of the double bonds in the fatty acids. Thus, the beneficial properties of the unsaturated oil are substituted by the highly undesirable adverse properties of the saturated fats.

It would be desirable to provide a composition for applying flavoring to a food, which is easy to prepare, has an even-flavor distribution, but does not contain saturated fats.

It would be further desirable to provide a method for making flavored food, which is easy to prepare, has an even-flavor distribution, but does not contain saturated fats.

It would be further desirable if this method for applying flavoring were applicable to foods, such as popcorn, pastry, vegetables, potatoes, pasta, rice, fish or meats.

Especially desirable is a composition and method for applying oil and optionally flavoring components to popcorn for mass production and microwave popping systems. Popcorn is a food product which requires very careful handling in order to ensure large tender kernels when popped. It is a well-known fact that unless precautions are taken to preserve the moisture in the raw corn, it soon dries out, after which no popping method produces a satisfactory product. Oil coating is known to preserve moisture, and obviously, an even distribution of the oil is essential to protect the whole mass of the corn. It is also accepted that the proportion between oil and corn affects the results obtained. Too little oil results in small kernels, whereas too much oil results in soggy corn with inferior smell and taste.

The most common sources of oil for popping popcorn are coconut oil or liquid vegetable oils, which contain a high degree of un-saturation, e.g., corn oil, soybean oil, and certain partially hydrogenated edible oils like cottonseed.

Trends in the state of the art in the popping of corn have been to make the total operation simpler. This has involved attempts to put together in a single package more than one of the ingredients. For instance, U.S. Pat. No. 2,604,407 teaches that it is possible to preserve moisture in popcorn kernels by coating the kernels with the correct amount of liquid fat (vegetable oil) in such manner that homogeneous parcels with the correct amounts of corn and oil may be obtained for individual use, however, this method cannot ensure avoidance of oil spillage. U.S. Pat. No. 2,518,247 teaches the use of a total combined package of popcorn, oil (used as binder), salt, color, and flavoring.

There have been many attempts to improve the even distribution of oil-flavor systems on corn, by using partially or fully hydrogenated oils, which, due to the hydrogenation process, become semi-solids (examples are found in U.S. Pat. Nos. 4,163,066 and 4,888,186). Yet, because of this chemical transformation, the oils become saturated and lose their healthy properties.

The Food and Drug Administration has recently stated that consumption of such saturated oils, which contain "trans"-fatty acids contributes to increased blood LDL-cholesterol ("bad" cholesterol) levels, which increase the risk of coronary heart disease (U.S. Department of Health and Human Services, Press Release, Nov. 12, 3699). Blends of fats from animal and vegetable sources have also been used for this purpose (U.S. Pat. No. 5,514,407).

SUMMARY OF THE INVENTION

The present invention provides food products and methods for producing such food products. This invention provides: (1) a vehicle for combining the ingredients required to produce acceptable food in which a homogeneous distribution of the ingredients will allow a simplification of commercial operations; (2) a food product that is easy to use and to eliminate the possibility of oil spills in comparison with liquids oils currently in use for food production; (3) acceptable food products prepared from a process which enables the use of thixotropic compositions comprising intact unsaturated oils, which carry the healthy properties of such oils; (4) an oil-flavor system for food production, wherein salt and other flavoring particles are substantially distributed throughout a thixotropic composition, which is amenable to facile application to food materials or products; (5) a process for producing a food product comprising an oil coating, wherein such a good product can benefit from being coated by an oil which enhances food preservation or protection and which comprises the health benefits of unsaturated oils.

According to the present invention, there are herein provided food products containing unsaturated oils prepared from the incorporation of a thixotropic composition with a food material, said composition comprising an edible unsaturated oil in combination with an edible solidifying agent. In one embodiment said agent converting said oil into a thixotropic composition exhibiting both an at least semi-solid state upon standing and a liquid state upon being mechanically disturbed.

In one embodiment, said edible solidifying agent comprises a compound having a molecular weight of at least 200, having at least 1 hydroxyl group and converting said oil into a thixotropic composition exhibiting both an at least semi-solid state upon standing and a liquid state upon being mechanically disturbed.

In preferred embodiments of the present invention, said edible solidifying agent comprises at least one fatty alcohol derivative, having at least 15 carbon atoms in its carbon chain.

In preferred embodiments, the food product further comprises a raw food material or food product. The food material or food product may be selected from the group consisting of fresh, processed, or pre-cooked starch, carbohydrate, protein, fats, potatoes, wheat, corn, barley, oats, rye, millet, vegetables, fruit, tubers, nuts, legumes, seeds, rice, fish, eggs, milk, cheese, meats, poultry, and mixtures thereof. Thus the invention provides for a food product wherein a raw or unprocessed food material selected from one of the food groups is mixed, coated, layered, or otherwise supplemented with said thixotropic composition comprising an edible unsaturated oil in combination with an edible solidifying agent. Likewise, the invention provides for a food product wherein a cooked, fried, baked, steamed, boiled, or otherwise cooked or processed food material or food product is mixed, coated, layered, or otherwise supplemented with said thixotropic composition comprising an edible unsaturated oil in combination with an edible solidifying agent.

In especially preferred embodiments of the present invention, said composition further comprises an edible flavoring, colorant, or nutrient component.

In accordance with the present invention there is also provided a process of producing a food product, wherein a thixotropic composition in liquid state is applied to a food material or product to produce a food product comprising said thixotropic composition, wherein said composition is prepared by blending an edible unsaturated oil in combination with an edible solidifying agent, at a temperature above the melting point of said solidifying agent, to produce said thixotropic composition exhibiting both a liquid state upon being mechanically disturbed and an at lest semi-solid state upon standing. Thus provided is a method of preparing food containing a variable proportion of unsaturated oil including the steps of preparing and using a thixotropic composition comprising said oil.

DETAILED DESCRIPTION OF THE INVENTION

A thixotropic composition has the property of exhibiting both an at least semi-solid state upon standing and a liquid state upon being mechanically disturbed. This property allows for application to an article of a thixotropic mixture as a liquid, which subsequently becomes substantially more solid and therefore more adherent to the article. Food products comprising and prepared from thixotropic mixtures comprising a high proportion of unsaturated oils are provided for herein.

An important feature of the present invention relates to the flow properties of the composition used to prepare food products comprising, or coated with, unsaturated oil. Viscosity is the most commonly known term that describes flow properties. Often used as a single parameter to characterize materials, the viscosity that a product should have for a specific application is a complex topic. The term thixotropic describes a full-bodied or solid-like material which undergoes a reduction in viscosity when shaken, stirred or otherwise mechanically disturbed but which readily recovers its original full-bodied condition upon standing. Low viscosity is recommended for easy spreading, but higher viscosity provides layer thickness for better coverage and conservation of mixture integrity.

The thixotropic composition for use in the present invention may be formed by blending an edible unsaturated oil in combination with an edible solidifying agent, at a temperature above the melting point of said solidifying agent, to produce said thixotropic composition exhibiting both an at least semi-solid state upon standing and a liquid state upon being mechanically disturbed. Selected examples of said thixotropic composition are the compositions obtained upon adding 4 gr. of behenyl alcohol to 1000 gr. of soybean oil and stirring the mixture to 180 C. until the alcohol is completely dissolved in the oil; or adding 2 gr. of stearyl alcohol to 97 gr. of olive oil and stirring the mixture at 60 C.; or adding 0.2 gr. of cetyl alcohol to 9.8 gr. of canola oil at 60 C. One skilled in the art will readily appreciate the oil-alcohol combinations and blending conditions required for the formation of the thixotropic composition comprising unsaturated oils which is a feature of the food products and process for preparation thereof disclosed herein.

The process for food preparation disclosed herein utilizes a thixotropic composition comprising unsaturated oils. When agitated at ambient temperature it has low viscosity, allowing facile application onto food by pouring, sprinkling or spraying. Soon after application it becomes very viscous, which eliminates dripping and sedimentation of flavor and therapeutic additives. Thus, the thixotropic composition of the present invention is better than conventional saturated fat compositions, which solidify gradually, thus requiring high temperature in order to facilitate application onto a food product and homogeneous distribution on the food and chilling in order to conserve consistency.

Moreover, according to the method of the present invention, the chemical structure of the unsaturated oils is not changed, and therefore the health benefits, which are attributed to such oils are conserved, thus providing an alternative for current methods, which involve hydrogenation, yielding saturated fats, which carry untoward health risks.

One aspect of the present invention is to provide an effective, homogeneous oil-flavor coating of frozen food. Oils, such as olive oil and different flavoring agents often flavor such foods. Yet, it is technically difficult to apply oils and flavors on foods and to ensure that the oil does not drip from the food to the bottom of the package, prior to freezing. The composition and method of the present invention provide a technical solution for the above problem. When the thixotropic oil-flavor system is applied onto foods, by sprinkling, dipping or brushing, uniform distribution of the oil and flavoring is attained and no spillage occurs.

The composition of the present invention includes edible unsaturated oils, the concentration of which is variable, ranging between 20–40%; 30–50%; 40–60%; 50–70%; 60–80%; 70–90%; or 80–99.8%. More preferably, it is 60 to about 99.8% or 75 to about 99.8%. Preferably they are selected from a variety of oils from vegetable or marine sources.

By way of example, the unsaturated oil maybe selected from the group consisting of olive, corn, soybean, canola, cottonseed, coconut, sesame, sunflower, borage seed, *syzigium aromaticum*, hempseed, herring, cod-liver, salmon, flaxseed, wheat germ and evening primrose oils and mixtures thereof, at any proportion.

A particularly preferred class of oils includes polyunsaturated oils, containing omega-3 and omega-6 fatty acids. Thus, in an especially preferred embodiment of the present invention said unsaturated oil contains at least 6% of an oil selected from omega-3 oil, omega-6 oil, and mixtures thereof.

Preferred solidifying agents, according to the present invention include fatty alcohols having 15 or more carbons in their carbon chain, such as cetyl alcohol and stearyl alcohol (or mixtures thereof), which are allowed for human ingestion without restriction (U.S. Food and Drug Administration, Center for Food Safety & Applied Nutrition; EAFUS: A Food Additive Database). Other examples of fatty alcohols are arachidyl alcohol (C20), behenyl alcohol (C22), 1-triacontanol (C30), as well as alcohols with longer carbon chains (up to C50). The concentration of the fatty alcohol, required to obtain a thixotropic oil-flavor system is inversely related to the length of its carbon chains.

Preferably, said edible solidifying agent has a molecular weight of at least 200, has at least 1 hydroxyl group, and converts said combination of said oil and said solidifying agent into said thixotropic composition.

Fatty alcohols, derived from beeswax, comprising an mixture of alcohols, a majority of which has at least 20 carbon atoms in their carbon chain are especially well suited as solidifying agents according to the present invention.

Furthermore, said solidifying agent can be a component of a natural product such as beeswax, which can be used per se without the separation of the fatty alcohols therefrom.

Thus, in preferred embodiments of the present invention said solidifying agent comprises beeswax or a mixture of fatty alcohols derived from beeswax, a majority of said fatty alcohols having at least 20 carbon atoms in their carbon chains.

Another class of solidifying agent according to the present invention comprises an edible di-alcohol, having formula A or B as follows:

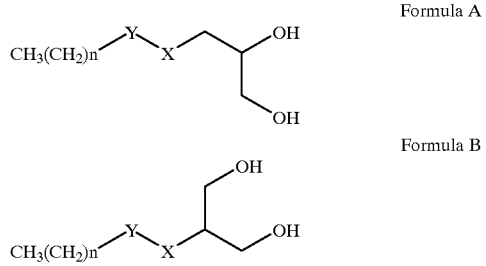

wherein, n=8–48;
X=CHR, O, or NH;
Y=CHR; or C=O; and
R=H or alkyl.

Monoglycerides of long chain fatty acids, e.g., glycerol monostearate and glycerol monopalmitate are suitable examples of this class of solidifying agents. Monoglycerides have been reported in the literature to produce thixotropy in water-containing formulation, but not in compositions that contain oil as a main ingredient.

In a preferred embodiment of the present invention said thixotropic oil composition further comprises flavoring substances including water soluble, oil soluble and particulate flavors, commonly used for flavoring foods. In a similar fashion, colorants and odorants may be included in the thixotropic mixture, to produce a food product with enhanced appeal.

In another preferred embodiment of the present invention said thixotropic composition further comprises therapeutic agents. By way of example, therapeutic agents, suitable for inclusion in the edible thixotropic composition of the present invention may include Vitamin A, C, D, E, B1 (thiamine), B2 (riboflavin), niacine, nicotinamide, B6 (pyridoxine), B12, folic acid, biotin, panthothenic acid. They may also include minerals, such as sodium, calcium, iron, iodine, magnesium, zinc, selenium, copper, manganese, chromium and vanadium, any of them as inorganic salts or organo-metallic complexes. They may further comprise powdered medicinal herbs or herbal extract of aloe vera, anise, balm, baneberry, basil, thyme, bearberry, bloodroot, cedar, chamomile, chicory, cloves, echinacea, fennel, feverfew, garlic, ginseng, hors nettle, ivy, juniper, lavender, horse nettle, onion, parsley, peppermint, rosemary, sage/saw palmetto berries, St. John's wort, senna, thyme, valerian, yarrow, as well as other herbs known in the art of herbal medicine. Such therapeutic additives may be included at amounts of up to 20 times their respective recommended daily dose, per serving unit (when applicable). Therapeutic agents according to the present invention may also consist of a prescription of non-prescription drug substance (hereinafter referred to as a medication). Incorporating a medication in the present thixotropic oil composition, provides a novel delivery methods for such patients who cannot swallow pills and capsules, due to physiological limitations.

Thus the present invention, in its especially preferred embodiments, concerns a thixotropic composition for applying flavoring to a food, comprising an edible unsaturated oil, an edible solidifying agent as defined and an edible flavoring, colorant, odorant, nutritive, or medicinal component. The composition, being solid at room temperature, provides substitute for currently used saturated fats, which carry untoward health risks.

In another aspect of the present invention, there is provided a method for producing a food product comprising:
(a) preparing a thixotropic oil-flavor system, by blending a major portion of an edible unsaturated oil and an edible-flavor component, in combination with an edible solidifying agent, said agent having a molecular weight of at least 200, having at least 1 hydroxyl group and converting said oil into a thixotropic composition exhibiting both an at least semi-solid state upon standing and a liquid state upon being mechanically disturbed, at a temperature above the melting point of said solidifying agent;
(b) applying said oil-flavor system in liquid state to a food material or product; and
(c) maintaining said oil-flavor system in liquid state in contact with said food material or product for a time sufficient to permit at least a portion of said oil-flavor system to adhere to said food material or product, to produce a food product comprising said thixotropic composition.

Thus, the present invention further concerns a method for applying flavoring to a food by preparing an oil-flavor mixture, having thixotropic properties and applying it on a food. The method is simple and convenient, produces an even flavor distribution, and in contrast to prior known methods for applying flavorings, does not require applying the flavoring while cooking the food in a liquid fat.

As described hereinbefore, an oil-flavor system, having thixotropic properties, is prepared by blending an edible unsaturated oil, an edible solidifying agent as defined herein and edible flavoring, at temperature above the melting point of the solidifying agent. The oil-flavor system is applied to the base food, for example, by shaking thereon sprinkling or spraying. The oil-flavor system is maintaining said oil-flavor system in contact with said base food for a time sufficient to permit at least a portion of said oil-flavor system to adhere to said base food.

In a preferred embodiment, the method is useful for producing flavored pastry, vegetables, potatoes, pasta, rice, or meats having an evenly distributed flavor, using the thixotropic oil-flavor system of the present invention. The thixotropic oil-flavor system preferably contains 75 to 99.8% by weight of one or more non-hydrogenated, unsaturated vegetable oils, such as of olive, soybean, canola, cottonseed, coconut, sesame, cod-liver, salmon, flaxseed, wheat germ, corn, primrose and mixtures thereof.

In another preferred embodiment, the method is useful for producing flavored popcorn having an evenly distributed flavor, using the thixotropic oil-flavor system of the present invention. Thus, in accordance with the present invention there is provided a composition for popping popcorn comprising a thixotropy oil-flavor system as defined herein, having salt and other flavoring particles substantially homogeneously distributed throughout. Preferably, the composition also includes coloring and flavoring. The present invention provides a system which is improved from the following viewpoints: (1) to provide a vehicle for combining the ingredients required to produce acceptable popcorn in which a homogeneous distribution of the ingredients will allow a simplification of corn popping in commercial operations; (2) to provide a product that is easy to use and to eliminate the possibility of oil spills in comparison with liquid oils currently in use for the popping of corn and (3) to provide an oil composition for popping popcorn, containing intact unsaturated oils, which carry the healthy properties of such oils.

Yet, another object of the present invention is to provide an effective even oil-flavor coating of frozen food.

Thus, the present invention provides food products having a thixotropic unsaturated oil composition applied thereto, said composition comprising a major portion of an edible unsaturated oil in combination with an edible solidifying agent, said agent having a molecular weight of at least 200, having at least 1 hydroxyl group and converting said oil into a thixotropic composition exhibiting both an at least semi-solid state upon standing and a liquid state upon being mechanically disturbed.

As stated, in especially preferred embodiments of the present invention, said agent comprises at least one fatty alcohol derivative, having at least 15 carbon atoms in its carbon chain.

Preferably, said food product is selected from the group consisting of popcorn, pastry, vegetables, potatoes, pasta, rice, meats and mixtures thereof.

In a further preferred embodiment, the method is useful for delivering therapeutic substances, otherwise difficult to deliver for oral consumption, by incorporating them in a thixotropic oil-flavor system, as defined herein. The thixotropic oil-flavor system, containing said therapeutic substances, is further applied onto foodstuff, selected from popcorn, pastry, vegetables, potatoes, pasta, rice, fish or meats and mixtures thereof.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

Thixotropic edible olive oil-flavor system

2gr. of stearyl alcohol was added to 97 gr. of olive oil and the mixture was stirred at 60° C. until the alcohol was completely dissolved in the oil. 0.3 gr. of garlic extract, 0.5 gr. salt and 0.2 gr. ground majoran were added to the hot mixture and the mixture was cooled off to 30° C. with stirring, then poured into containers and cooled to room temperature. A gelatin-like system was obtained, with taste and smell similar to the original olive oil. Upon shaking at 30° C., the gel became liquid and after application on food surface it became solid again.

Example 2

Thixotropic edible fish oil-flavor system

4gr. of beeswax-derived fatty alcohols was added to 96 gr. of cod liver oil and the mixture was stirred at 60° C. until the alcohols were completely dissolved in the oil. 0.5 gr. of lemon concentrate, 0.4 gr. salt, 0.1 gr. black pepper and 0.2 gr. ground garlic were added to the hot mixture and the mixture was cooled off to 30° C. with stirring, then poured into containers and cooled to room temperature. A gelatin-like system was obtained. Upon shaking at 30° C., the gel became liquid and after application on food surface it became solid again. GCMS analysis revealed that the lipid composition of the spread was identical to the original cod liver oil. The taste and smell of the resulting spread were distinctly different from the parent oil and were found acceptable by a panel of tasters.

Example 3

Thixotropic edible canola oil-flavor system with therapeutic agents 0.2 gr. of cetyl alcohol was added to 9.8 gr. of canola oil and the mixture was stirred at 60° C. until the alcohol was completely dissolved in the oil. Vitamins, minerals and herbs were added to the hot mixture in order to achieve the following composition:

| Vitamin A | 20,000 IU | Sodium chloride | 400 mg |
|---|---|---|---|
| Vitamin C | 1,000 mg | Calcium (as amino acid chelate) | 500 mg |
| Vitamin D | 800 IU | Iron (as ferrous fumarate) | 20 mg |
| Vitamin E | 400 IU | Iodine | 225 mcg |
| Vitamin B1 (thiamine) | 25 mg | Magnesium (as amino acid chelate) | 250 mg |
| Vitamin B2 (riboflavin) | 25 mg | Zinc (as amino acid chelate) | 25 mg |
| Niacin | 150 mg | Selenium (as Selenomethionine) | 25 mcg |
| Nicotinamide | 150 mg | Copper (as amino acid chelate) | 2 mg |
| Vitamin B6 (pyridoxine) | 30 mg | Manganese (as amino acid chelate) | 10 mg |
| Vitamin B12 | 50 mcg | Chromium picolinate | 1,000 mcg |
| Folic acid | 400 mcg | Potassium (as amino acid chelate) | 50 mg |
| Biotin | 150 mcg | Inositol | 100 mg |
| Panthothenic acid | 150 mg | | |

The mixture was cooled off to 30° C. with stirring, then poured into containers and cooled to room temperature. A gelatin-like system was obtained. Upon shaking at 30° C., the gel became liquid and after application on food surface it became solid again.

Example 4

Thixotropic edible chocolate-flavored primrose oil spread

4gr. of beeswax-derived fatty alcohols was added to 96 gr. of primrose oil and the mixture was stirred at 60° C. until the alcohols were completely dissolved in the oil. 8 gr. cacao powder, 10 gr. sugar* and 5 gr. powdered milk were added and the mixture was cooled off with stirring to 30° C. with stirring, then poured into containers and cooled to room temperature. A tasty chocolate flavored thixotropic gel was obtained. It was used to coat different kinds of pastry products and was well accepted by the consumers.

*10 gr. sugar could be substituted by 0.2 gr. saccharine or 0.2 gr. aspartame.

Example 5

Popcorn 0.7 gr. of beeswax-derived fatty alcohols and 0.5 gr. salt was added to 18 gr. of canola oil and the mixture was stirred at 60° C. until the alcohols were completely dissolved in the oil. The mixture was cooled off with stirring to 30° C. Then 100 gr. of corn grains were added and mixed together with the oil-flavor system, until the grains were uniformly coated with oil, which was apparently solid. The mixture was filled into a paper bag and placed in the microwave for 4 minutes, at high level energy. At the end of this period, all grains were popped and the kernels were large and crispy.

Example 6

Sweet popcorn

The same method as in Example 5 was applied, but instead of salt, 5 gr. sugar was added to the oil system. 50 gr. of corn grains, coated with oil-sugar, were placed in a hot pot and allowed to pop (about 3 minutes). Large, off-white, crispy and sweet popcorn kernels were obtained.

Example 7

Flavored pasta—comparative study

Italian-style pasta was prepared by mixing cooked pasta with the oil-flavor system of example 1, and a ratio of 900 gr. pasta and 100 gr. oil-flavor system. The mixture was then divided to four 250 gr. containers and 10 minutes afterwards, they were stored in the freezer at −4° C.—8° C. for 8 weeks. A control product, consisting of 900 gr. pasta, 97 gr. olive oil, 0.3 gr. garlic extract, 0.5 gr. salt and 0.2 gr. of ground majoran, was prepared by mixing all ingredients in the same manner and for the same time, divided to 250 gr. containers and stored in the freezer. At the end of storage, the pasta, treated with the oil-flavor system was uniformly coated with oil and only a minute amount of oil was found at the bottom of the container. In contrast, in each of the containers of the control product, the top layers of the pasta were virtually dry and about 15 gr. Oil was found at the bottom of the container. Likewise, most of the majoran was found at the bottom of the control containers.

Example 8

Pre-fried potato chips 4 gr. of behenyl alcohol and was added to 1000 gr. of soybean oil and the mixture was heated to 180 C. The 100 gr. of fresh potato chips were added and fried for 2 minutes. The potato chips were removed from the oil and immediately stored at −20 C. The resulting product was similar in consistency to reference product, which was produced using conventional shortening. Yet the saturated oil content was similar to the original soybean oil.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What we claim is:

1. A food product comprising a thixotropic composition wherein said thixotropic composition comprising a portion of an edible unsaturated oil in combination with an edible solidifying agent, said agent converting said combination of said oil and said solidifying agent into said thixotropic composition, wherein said solidifying agent comprising an edible di-alcohol, said di-alcohol being selected from the group having the formula A:

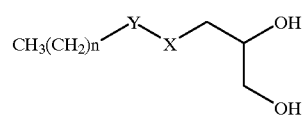

Formula A wherein, N=8–48;
X=CHR, O, or NH;
Y=CHR; or C=O; and
R=H or alkyl.

2. The food product of claim 1, wherein said thixotropic composition comprising an edible flavoring, colorant, or odorant.

3. The food product of claim 1, wherein said unsaturated oil is present in a concentration within the range of 70–99.8 percent by weight.

4. The food product of claim 1, wherein said unsaturated oil is of vegetable or marine origin.

5. The food product of claim 1, wherein said unsaturated oil is selected from the group consisting of olive, soybean, canola, cottonseed, coconut, sesame, sunflower, borage seed, *syzigium aromaticum*, hempseed, herring, cod-liver, salmon, corn, flaxseed, wheat germ and evening primrose oils and mixtures thereof.

6. The food product of claim 1, wherein said unsaturated oil comprises a major portion of poly-unsaturated oils.

7. The food product of claim 1, wherein said thixotropic composition comprising an edible flavoring, wherein said flavoring is selected from the group consisting of sugar, salt, pepper and cumin.

8. The food product of claim 1 wherein said thixotropic composition comprising at least one therapeutic agent in an amount up to 20 times the recommended daily dose per serving unit.

9. The food product of claim 1 wherein said thixotropic composition comprising at least one therapeutic agent, selected from the group consisting of vitamin A, vitamin C, vitamin D, vitamin E, vitamin B1 (thiamine), vitamin B2 (riboflavin), niacine, nicotinamide, vitamin B6 (pyridoxine), vitamin B12, folic acid, biotin, panthothenic acid, inorganic salts or organo-metallic complexes of sodium, calcium, iron, iodine, magnesium, zinc, selenium, copper, manganese, chromium and vanadium, powder or extracts of aloe vera, anise, balm, baneberry, basil, thyme, bearberry, bloodroot, cedar, chamomile, chicory, cloves, echinacea, fennel, feverfew, garlic, ginseng, horse nettle, ivy, juniper, lavender, horse nettle, onion, parsley, peppermint, rosemary, sage, saw palmetto berries, St. John's wort, senna, thyme, valerian and yarrow, and mixtures thereof, in an amount up to 20 times the recommended daily dose per serving unit.

10. The food product of claim 1, wherein said thixotropic composition comprising a medication.

11. The food product of claim 1, wherein said unsaturated oil consisting of at least 6% of an oil selected from omega-3 oil, omega-6 oil, and mixtures thereof.

12. The food product of claim 1, wherein said food product further comprises a food material or product selected from the group consisting of fresh, processed, or pre-cooked starch, carbohydrate, protein, fats, potatoes, wheat, corn, barley, oats, rye, millet, vegetables, fruit, tubers, nuts, beans, seeds, rice, fish, eggs, milk, cheese, meats poultry and mixtures thereof.

13. The food product of claim 1, wherein said food product further comprises a food material or product selected from the group consisting of fresh, processed, or pre-cooked popcorn, pastry, breads, baked goods, pasta, batter, crackers, potato chips, tortilla, snack foods, confections, comestibles and mixtures thereof.

14. The food product of claim 1, wherein said food product further comprises a food material or product selected from the group consisting of pre-fried foodstuff including potato chips, tortilla, and mixtures thereof.

15. A food product having a thixotropic unsaturated oil composition applied thereto, said composition comprising an edible unsaturated oil in combination with an edible solidifying agent, said agent converting said combination of said oil and said solidifying agent into said thixotropic composition, wherein said solidifying agent comprising an edible di-alcohol, said di-alcohol being selected from the group having the formula A:

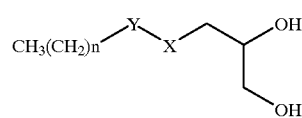

Formula A wherein, n=8–48;
X=CHR, O, or NH;
Y=CHR; or C=O; and
R=H or alkyl.

16. A food product of claim 15, wherein said thixotropic composition comprising an edible flavoring, colorant, or odorant.

17. A food product of claim 15, wherein said unsaturated oil is present in a concentration within the range of 70–99.8 percent by weight.

18. A food product of claim 15, wherein said unsaturated oil is of vegetable or marine origin.

19. A food product of claim 15, wherein said unsaturated oil is selected from the group consisting of olive, soybean, canola, cottonseed, coconut, sesame, sunflower, borage seed, *syzigium aromaticum*, hempseed, herring, cod-liver, salmon, corn, flaxseed, wheat germ and evening primrose oils and mixtures thereof.

20. A food product of claim 15, wherein said unsaturated oil comprising a major portion of poly-unsaturated oils.

21. A food product of claim 15, wherein said thixotropic composition comprising an edible flavoring, wherein said flavoring is selected from the group consisting of sugar, salt, pepper and cumin.

22. A food product of claim 15 wherein said thixotropic composition comprising at least one therapeutic agent in an amount up to 20 times the recommended daily dose per serving unit.

23. A food product of claim 15 wherein said thixotropic composition comprising at least one therapeutic agent, selected from the group consisting of vitamin A, vitamin C, Vitamin D, vitamin E, vitamin B1 (thiamine), vitamin B2 (riboflavin), niacine, nicotinamide, vitamin B6 (pyridoxine), vitamin B12, folic acid, biotin, panthothenic acid, inorganic salts or organo-metallic complexes of sodium, calcium, iron, iodine, magnesium, zinc, selenium, copper, manganese, chromium and vanadium, powder or extracts of aloe vera, anise, balm, baneberry, basil, thyme, bearberry, bloodroot, cedar, chamomile, chicory, cloves, echinacea, fennel, feverfew, garlic, ginseng, horse nettle, ivy, juniper, lavender, horse nettle, onion, parsley, peppermint, rosemary, sage, saw palmetto berries, St. John's wort, senna, thyme, valerian and yarrow, and mixtures thereof, in an amount up to 20 times the recommended daily dose per serving unit.

24. A food product of claim 15 wherein said thixotropic composition comprising a medication.

25. A food product of claim 15, wherein said unsaturated oil consisting of at least 6% of an oil selected from omega-3 oil, omega-6 oil, and mixtures thereof.

26. A food product of claim 15, wherein said food product is selected from the group consisting of fresh, processed, or pre-cooked starch, carbohydrate, protein, fats, potatoes, wheat, corn, barley, oats, rye, millet, vegetables, fruit, tubers, nuts, legumes, seeds, rice, fish, eggs, milk, cheese, meats, poultry and mixtures thereof.

27. A food product of claim 15, wherein said food product is selected from the group consisting of fresh, processed, or pre-cooked popcorn, pastry, breads, baked goods, pasta, batter, crackers, tortilla, snack foods, confections, comestibles and mixtures thereof.

28. A food product of claim 15, wherein said food product is selected from the group consisting of pre-fried foodstuff including potato chips, tortilla, and mixtures thereof.

29. A process of producing a food product, wherein said food product comprising a thixotropic composition wherein said thixotropic composition comprising an edible unsaturated oil in combination with an edible solidifying agent, said converting said combination of said oil and said solidifying agent into said thixotropic composition, said process comprising the steps of:

(a) preparing said thixotropic composition, by blending a major portion of an edible unsaturated oil in combination with said edible solidifying agent to produce said thixotropic composition exhibiting both an at least semi-solid state upon standing and a liquid state upon being mechanically disturbed, at a temperature above the melting point of said solidifying agent, wherein said solidifying agent comprising an edible di-alcohol, said di-alcohol being selected from the group having the formula A:

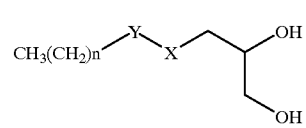

Formula A wherein, n=8–48;
X=CHR, O, or NH;
Y=CHR; or C=O; and
R=H or alkyl;

(b) applying said thixotropic composition in liquid state to a food material or product; and (c) maintaining said thixotropic composition in liquid state in contact with said food material or product for a time sufficient to permit at least a portion of said thixotropic composition to adhere to said food material or product, to produce a food product comprising said thixotropic composition.

30. The process of claim 29 wherein said step (b) comprising applying the said thixotropic composition to surfaces of the food material or product so as to achieve a fairly uniform distribution of said thixotropic composition thereupon.

31. The process of claim 29, wherein said thixotropic composition comprising an edible flavoring, colorant, or odorant.

32. The process of claim 29, wherein said unsaturated oil is present in a concentration within the range of 70–99.8 percent by weight.

33. The process of claim 29, wherein said unsaturated oil is of vegetable or marine origin.

34. The process of claim 29, wherein said unsaturated oil is selected from the group consisting of olive, soybean, canola, cottonseed, coconut, sesame, sunflower, borage seed, *syzigium aromaticum*, hempseed, herring, cod-liver, salmon, corn, flaxseed, wheat germ and evening primrose oils and mixtures thereof.

35. The process of claim 29, wherein said unsaturated oil comprising a major portion of poly-unsaturated oils.

36. The process of claim 29, wherein said thixotropic composition comprising an edible flavoring, wherein said flavoring is selected from the group consisting of sugar, salt, pepper and cumin.

37. The process of claim 29, wherein said thixotropic composition comprising at least one therapeutic agent in an amount up to 20 times the recommended daily dose per serving unit.

38. The process of claim 29, wherein said thixotropic composition comprising at least one therapeutic agent, selected from the group consisting of vitamin A, vitamin C, vitamin D, vitamin E, vitamin B1 (thiamine), vitamin B2 (riboflavin), niacine, nicotinamide, vitamin B6 (pyridoxine), vitamin B12, folic acid, biotin, panthothenic acid, inorganic salts or organo-metallic complexes of sodium, calcium, iron, iodine, magnesium, zinc, selenium, copper, manganese, chromium and vanadium, powder or extracts of aloe vera, anise, balm, baneberry, basil, thyme, bearberry, bloodroot, cedar, chamomile, chicory, cloves, echinacea, fennel, feverfew, garlic, ginseng, horse nettle, ivy, juniper, lavender, horse nettle, onion, parsley, peppermint, rosemary, sage, saw palmetto berries, St. John's wort, senna, thyme, valerian and yarrow, and mixtures thereof, in an amount up to 20 times the recommended daily dose per serving unit.

39. The process of claim 29, wherein said thixotropic composition comprising a medication.

40. The process of claim 29, wherein said unsaturated oil consisting of at least 6% of an oil selected from omega-3 oil, omega-6 oil, and mixtures thereof.

41. The process of claim 29, wherein said food material or product is selected from the group consisting of fresh, processed, or pre-cooked starch, carbohydrate, protein, fats, potatoes, wheat, corn, barley, oats, rye, millet, vegetables, fruit, tubers, nuts, legumes, seeds, rice, fish, eggs, milk, cheese, meats, poultry and mixtures thereof.

42. The process of claim 29, wherein said food material or product is selected from the group consisting of fresh, processed, or pre-cooked popcorn, pastry, breads, baked goods, pasta, batter, crackers, tortilla, snack foods, confections, comestibles and mixtures thereof.

43. The process of claim 29, wherein said food material or product is selected from the group consisting of pre-fried foodstuff including potato chips, tortilla, and mixtures thereof.

44. A food product comprising a thixotropic composition wherein said thixotropic composition comprising a portion of an edible unsaturated oil in combination with an edible solidifying agent, said agent converting said combination of said oil and said solidifying agent into said thixotropic composition, wherein said solidifying agent comprising an edible di-alcohol, said di-alcohol being selected from the group having the formula B:

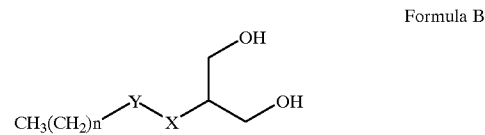

Formula B wherein, n=8–48;
X=CHR, O, or NH;
Y=CHR; or C=O; and
R=H or alkyl.

45. The food product of claim 44, wherein said thixotropic composition comprising an edible flavoring, colorant, or odorant.

46. The food product of claim 44, wherein said unsaturated oil is present in a concentration within the range of 70–99.8 percent by weight.

47. The food product of claim 44, wherein said unsaturated oil is of vegetable or marine origin.

48. The food product of claim 44, wherein said unsaturated oil is selected from the group consisting of olive, soybean, canola, cottonseed, coconut, sesame, sunflower, borage seed, *syzigium aromaticum*, hempseed, herring, cod-liver, salmon, corn, flaxseed, wheat germ and evening primrose oils and mixtures thereof.

49. The food product of claim 44, wherein said unsaturated oil comprises a major portion of poly-unsaturated oils.

50. The food product of claim 44, wherein said thixotropic composition comprising an edible flavoring, wherein said flavoring is selected from the group consisting of sugar, salt, pepper and cumin.

51. The food product of claim 44 wherein said thixotropic composition comprising at least one therapeutic agent in an amount up to 20 times the recommended daily dose per serving unit.

52. The food product of claim 44 wherein said thixotropic composition comprising at least one therapeutic agent, selected from the group consisting of vitamin A, vitamin C, vitamin D, vitamin E, vitamin B1 (thiamine), vitamin B2 (riboflavin), niacine, nicotinamide, vitamin B6 (pyridoxine), vitamin B12, folic acid, biotin, panthothenic acid, inorganic salts or organo-metallic complexes of sodium, calcium, iron, iodine, magnesium, zinc, selenium, copper, manganese, chromium and vanadium, powder or extracts of aloe vera, anise, balm, baneberry, basil, thyme, bearberry, bloodroot, cedar, chamomile, chicory, cloves, echinacea, fennel, feverfew, garlic, ginseng, hose nettle, ivy, juniper, lavender, horse nettle, onion, parsley, peppermint, rosemary, sage, saw palmetto berries, St. John's wort, senna, thyme, valerian and yarrow, and mixtures thereof, in an amount up to 20 times the recommended daily dose per serving unit.

53. The food product of claim 44, wherein said thixotropic composition comprising a medication.

54. The food product of claim 44, wherein said unsaturated oil consisting of at least 6% of an oil selected from omega-3 oil, omega-6 oil, and mixtures thereof.

55. The food product of claim 44 wherein said food product further comprises a food material or product selected from the group consisting of fresh, processed, or pre-cooked starch, carbohydrate, protein, fats, potatoes, wheat, corn, barley, oats, rye, millet, vegetables, fruit, tubers, nuts, beans, seeds, rice, fish, eggs, milk, cheese, meats, poultry and mixtures thereof.

56. The food product of claim 44, wherein said food product further comprises a food material or product selected from the group consisting of fresh, processed, or pre-cooked popcorn, pastry, breads, baked goods, pasta, batter, crackers, potato chips, tortilla, snack foods, confections, comestibles and mixtures thereof.

57. The food product of claim 44, wherein said food product further comprises a food material or product selected from the group consisting of pre-fried foodstuff including potato chips, tortilla, and mixtures thereof.

58. A food product having a thixotropic unsaturated oil composition applied thereto, said composition comprising an edible unsaturated oil in combination with an edible solidifying agent, said agent converting said combination of said oil and said solidifying agent into said thixotropic composition, wherein said solidifying agent comprising an edible di-alcohol, said di-alcohol being selected from the group having the formula B:

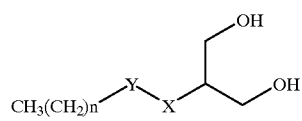

Formula B wherein, n=8–48;
X=CHR, O, or NH;
Y=CHR; or C=O; and
R=H or alkyl.

59. A food product of claim 58, wherein said thixotropic composition comprising an edible flavoring, colorant, or odorant.

60. A food product of claim 58, wherein said unsaturated oil is present in a concentration within the range of 70–99.8 percent by weight.

61. A food product of claim 58, wherein said unsaturated oil is of vegetable or marine origin.

62. A food product of claim 58, wherein said unsaturated oil is selected from the group consisting of olive, soybean, canola, cottonseed, coconut, sesame, sunflower, borage seed, *syzigium aromaticum*, hempseed, herring, cod-liver, salmon, corn, flaxseed, wheat germ and evening primrose oils and mixtures thereof.

63. A food product of claim 58, wherein said unsaturated oil comprising a major portion of poly-unsaturated oils.

64. A food product of claim 58 wherein said thixotropic composition comprising an edible flavoring, wherein said flavoring is selected from the group consisting of sugar, salt, pepper and cumin.

65. A food product of claim 58 wherein said thixotropic composition comprising at least one therapeutic agent in an amount up to 20 times the recommended daily dose per serving unit.

66. A food product of claim 58 wherein said thixotropic composition comprising at least one therapeutic agent, selected from the group consisting of vitamin A, vitamin C, vitamin D, vitamin E, vitamin B1 (thiamine), vitamin B2 (riboflavin), niacine, nicotinamide, vitamin B6 (pyridoxine), vitamin B12, folic acid, biotin, panthothenic acid, inorganic salts or organo-metallic complexes of sodium, calcium, iron, iodine, magnesium, zinc, selenium, copper, manganese, chromium and vanadium, powder or extracts of aloe vera, anise, balm, baneberry, basil, thyme, bearberry, bloodroot, cedar, chamomile, chicory, cloves, echinacea, fennel, feverfew, garlic, ginseng, horse nettle, ivy, juniper, lavender, horse nettle, onion, parsley, peppermint, rosemary, sage, saw palmetto berries, St. John's wort, senna, thyme, valerian and yarrow, and mixtures thereof, in an amount up to 20 times the recommended daily dose per serving unit.

67. A food product of claim 58 wherein said thixotropic composition comprising a medication.

68. A food product of claim 58, wherein said unsaturated oil consisting of at least 6% of an oil selected from omega-3 oil, omega-6 oil, and mixtures thereof.

69. A food product of claim 58, wherein said food product is selected from the group consisting of fresh, processed, or pre-cooked starch, carbohydrate, protein, fats, potatoes, wheat, corn, barley, oats, rye, millet, vegetables, fruit, tubers, nuts, legumes, seeds, rice, fish, eggs, milk, cheese, meats, poultry and mixtures thereof.

70. A food product of claim 58, wherein said food product is selected from the group consisting of fresh, processed, or pre-cooked popcorn, pastry, breads, baked goods, pasta, batter, crackers, tortilla, snack foods, confections, comestibles and mixtures thereof.

71. A food product of claim 58, wherein said food product is selected from the group consisting of pre-fried foodstuff including potato chips, tortilla, and mixtures thereof.

72. A process of producing a food product, wherein said food product comprising a thixotropic composition wherein said thixotropic composition comprising an edible unsaturated oil in combination with an edible solidifying agent, said converting said combination of said oil and said solidifying agent into said thixotropic composition, said process comprising the steps of:

(a) preparing said thixotropic composition, by blending a major portion of an edible unsaturated oil in combination with said edible solidifying agent to produce said thixotropic composition exhibiting both an at least semi-solid state upon standing and a liquid state upon being mechanically disturbed, at a temperature above the melting point of said solidifying agent, wherein said solidifying agent comprising an edible di-alcohol, said di-alcohol being selected from the group having the formula B:

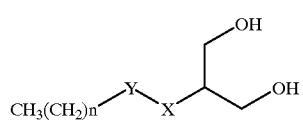

Formula B wherein, n=8–48;
X=CHR, O, or NH;
Y=CHR; or C=O; and
R=H or alkyl;

(b) applying said thixotropic composition in liquid state to a food material or product; and (c) maintaining said thixotropic composition in liquid state in contact with said food material or product for a time sufficient to permit at least a portion of said thixotropic composition to adhere to said food material or product, to produce a food product comprising said thixotropic composition.

73. The process of claim 72, wherein said step (b) comprising applying said thixotropic composition to surfaces of the food material or product so as to achieve a fairly uniform distribution of said thixotropic composition thereupon.

74. The process of claim 72, wherein said thixotropic composition comprising an edible flavoring, colorant, or odorant.

75. The process of claim 72, wherein said unsaturated oil is present in a concentration within the range of 70–99.8 percent by weight.

76. The process of claim 72, wherein said unsaturated oil is of vegetable or marine origin.

77. The process of claim 72, wherein said unsaturated oil is selected from the group consisting of olive, soybean, canola, cottonseed, coconut, sesame, sunflower, borage seed, pi syzigium aromaticum, hempseed, herring, cod-liver, salmon, corn, flaxseed, wheat germ and evening primrose oils and mixtures thereof.

78. The process of claim 72, wherein said unsaturated oil comprising a major portion of poly-unsaturated oils.

79. The process of claim 72, wherein said thixotropic composition comprising an edible flavoring, wherein said flavoring is selected from the group consisting of sugar, salt, pepper and cumin.

80. The process of claim 72, wherein said thixotropic composition comprising at least one therapeutic agent in an amount up to 20 times the recommended daily dose per serving unit.

81. The process of claim 72, wherein said thixotropic composition comprising at least one therapeutic agent, selected from the group consisting of vitamin A, vitamin C, vitamin D, vitamin E, vitamin B1 (thiamine), vitamin B2 (riboflavin), niacine, nicotinamide, vitamin B6 (pyridoxine), vitamin B12, folic acid, biotin, panthothenic acid, inorganic salts or organo-metallic complexes of sodium, calcium, iron, iodine, magnesium, zinc, selenium, copper, manganese, chromium and vanadium, powder or extracts of aloe vera, anise, balm, baneberry, basil, thyme, bearberry, bloodroot, cedar, chamomile, chicory, cloves, echinacea, fennel, feverfew, garlic, ginseng, horse nettle, ivy, juniper, lavender, horse nettle, onion, parsley, peppermint, rosemary, sage, saw palmetto berries, St. John's wort, senna, thyme, valerian and yarrow, and mixtures thereof, in an amount up to 20 times the recommended daily dose per serving unit.

82. The process of claim 72, wherein said thixotropic composition comprising a medication.

83. The process of claim 72, wherein said unsaturated oil consisting of at least 6% of an oil selected from omega-3 oil, omega-6 oil, and mixtures thereof.

84. The process of claim 72, wherein said food material or product is selected from the group consisting of fresh, processed, or pre-cooked starch, carbohydrate, protein, fats, potatoes, wheat, corn, barley, oats, rye, millet, vegetables, fruit, tubers, nuts, legumes, seeds, rice, fish, eggs, milk, cheese, meats, poultry and mixtures thereof.

85. The process of claim 72, wherein said food material or product is selected from the group consisting of fresh, processed, or pre-cooked popcorn, pastry, breads, baked goods, pasta, batter, crackers, tortilla, snack foods, confections, comestibles and mixtures thereof.

86. The process of claim 72, wherein said food material or product is selected from the group consisting of pre-fried foodstuff including potato chips, tortilla, and mixtures thereof.

* * * * *